(12) United States Patent
Pless et al.

(10) Patent No.: US 9,364,671 B2
(45) Date of Patent: Jun. 14, 2016

(54) NEUROMODULATION TO TREAT MENOPAUSE-RELATED CONDITIONS

(71) Applicant: Autonomic Technologies, Inc., Redwood City, CA (US)

(72) Inventors: Benjamin D. Pless, Atherton, CA (US); Shannon M. Schuetz, Shaker Hts., OH (US)

(73) Assignee: Autonomic Technologies, Inc., Redwood City, CA (US)

( * ) Notice: Subject to any disclaimer, the term of this patent is extended or adjusted under 35 U.S.C. 154(b) by 33 days.

(21) Appl. No.: 14/093,094

(22) Filed: Nov. 29, 2013

(65) Prior Publication Data
US 2014/0155956 A1 Jun. 5, 2014

Related U.S. Application Data

(60) Provisional application No. 61/730,630, filed on Nov. 28, 2012.

(51) Int. Cl.
*A61N 1/00* (2006.01)
*A61N 1/36* (2006.01)

(52) U.S. Cl.
CPC ........... *A61N 1/3606* (2013.01); *A61N 1/36157* (2013.01); *A61N 1/36171* (2013.01); *A61N 1/36175* (2013.01)

(58) Field of Classification Search
CPC   A61N 1/36139; A61N 1/3605; A61N 1/3606
USPC ....................................................... 607/59, 45
See application file for complete search history.

(56) References Cited

U.S. PATENT DOCUMENTS

| 2002/0116030 | A1* | 8/2002 | Rezai ................................ 607/9 |
| 2002/0120304 | A1* | 8/2002 | Mest ............................... 607/14 |
| 2006/0047325 | A1* | 3/2006 | Thimineur et al. ............. 607/45 |
| 2006/0079943 | A1* | 4/2006 | Narciso, Jr. ..................... 607/39 |
| 2008/0015659 | A1* | 1/2008 | Zhang et al. .................... 607/62 |

* cited by examiner

*Primary Examiner* — Christopher D Koharski
*Assistant Examiner* — Philip C Edwards
(74) *Attorney, Agent, or Firm* — Tarolli, Sundheim, Covell & Tummino LLP

(57) ABSTRACT

One aspect of the present disclosure relates to a method for treating a menopause-related condition in a subject. One step of the method can include inserting a therapy delivery device into a vessel of the subject. Next, the therapy delivery device can be advanced to a point substantially adjacent a target site of the sympathetic nervous system (SNS) that is associated with the menopause-related condition. The therapy delivery device can then be activated to deliver a therapy signal to the target site of the SNS in an amount and for a time sufficient to effect a change in sympathetic activity in the subject and thereby treat the menopause-related condition.

9 Claims, 4 Drawing Sheets

NEUROMODULATION TO TREAT MENOPAUSE-RELATED CONDITIONS

RELATED APPLICATION

This application claims the benefit of U.S. Provisional Patent Application Ser. No. 61/730,630, filed Nov. 28, 2012, the entirety of which is hereby incorporated by reference for all purposes.

TECHNICAL FIELD

The present disclosure relates generally to neuromodulatory devices, systems and methods, and more particularly to devices, systems, and methods for neuromodulation of the sympathetic nervous system to treat menopause-related conditions.

BACKGROUND

Hot flashes are experienced by many women undergoing menopause. A hot flash is a feeling of warmth, sometimes associated with flushing, that spreads over the body and may be accompanied by perspiration. Hot flashes may vary in severity and may last for a short period of time in some women, but can last for a decade or more in other women. Although the cause of hot flashes is not completely understood, hot flashes may be related to fluctuations of hormone levels experienced during menopause. Hot flashes also may be experienced secondary to mastectomy and other cancer-related treatments, particularly cancer treatments that affect hormone levels.

Traditionally, hot flashes have been treated with hormone therapy. Hormone replacement medications (usually estrogen or a combination of estrogen and progesterone) are effective in reducing the frequency of hot flashes and their severity. Generally, these medications decrease the frequency of hot flashes by about 80 to 90%. However, hormone replacement therapy is associated with increased risk of heart attack, stroke, blood clots, and breast cancer. Thus, alternative treatments are desirable.

Neuromodulation involves an array of therapeutic approaches applied to the brain, cranial nerves, spinal cord, and all associated nerves and neural structures in the human body to treat various human disorders. Neuromodulation can involve lesioning, electrical stimulation/modulation, and chemical stimulation/modulation, such as gene therapy and administration of stem cells. Electrical stimulation of neural tissue is becoming an increasingly preferred form of therapy for certain conditions and disorders where existing therapies generate intolerable side effects, require repeated administration of treatment, or are simply ineffective in a subset of patients.

SUMMARY

The present disclosure relates generally to neuromodulatory devices, systems and methods, and more particularly to devices, systems, and methods for neuromodulation of the sympathetic nervous system (SNS) to treat menopause-related conditions.

One aspect of the present disclosure relates to a method for treating a menopause-related condition in a subject. One step of the method can include inserting a therapy delivery device into a vessel of the subject. Next, the therapy delivery device can be advanced to a point substantially adjacent a target site of the SNS that is associated with the menopause-related condition. The therapy delivery device can then be activated to deliver a therapy signal to the target site of the SNS in an amount and for a time sufficient to effect a change in sympathetic activity in the subject and thereby treat the menopause-related condition.

Another aspect of the present disclosure relates to a method for treating a menopause-related condition in a subject. One step of the method can include placing a therapy delivery device, without penetrating the skin of the subject, into electrical communication with a target site of the SNS that is associated with the menopause-related condition. The therapy delivery device can then be activated to deliver a therapy signal to the target site of the SNS in an amount and for a time sufficient to effect a change in sympathetic activity in the subject and thereby treat the menopause-related condition.

Another aspect of the present disclosure relates to a method for treating a menopause-related condition in a subject. One step of the method can include implanting a therapy delivery device in the subject so that the therapy delivery device is in electrical contact with a target site of the SNS associated with the menopause-related condition. The therapy delivery device can then be activated to deliver a therapy signal to the target site of the SNS in an amount and for a time sufficient to effect a change in sympathetic activity in the subject and thereby treat the menopause-related condition.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

Definitions

Figure 1:
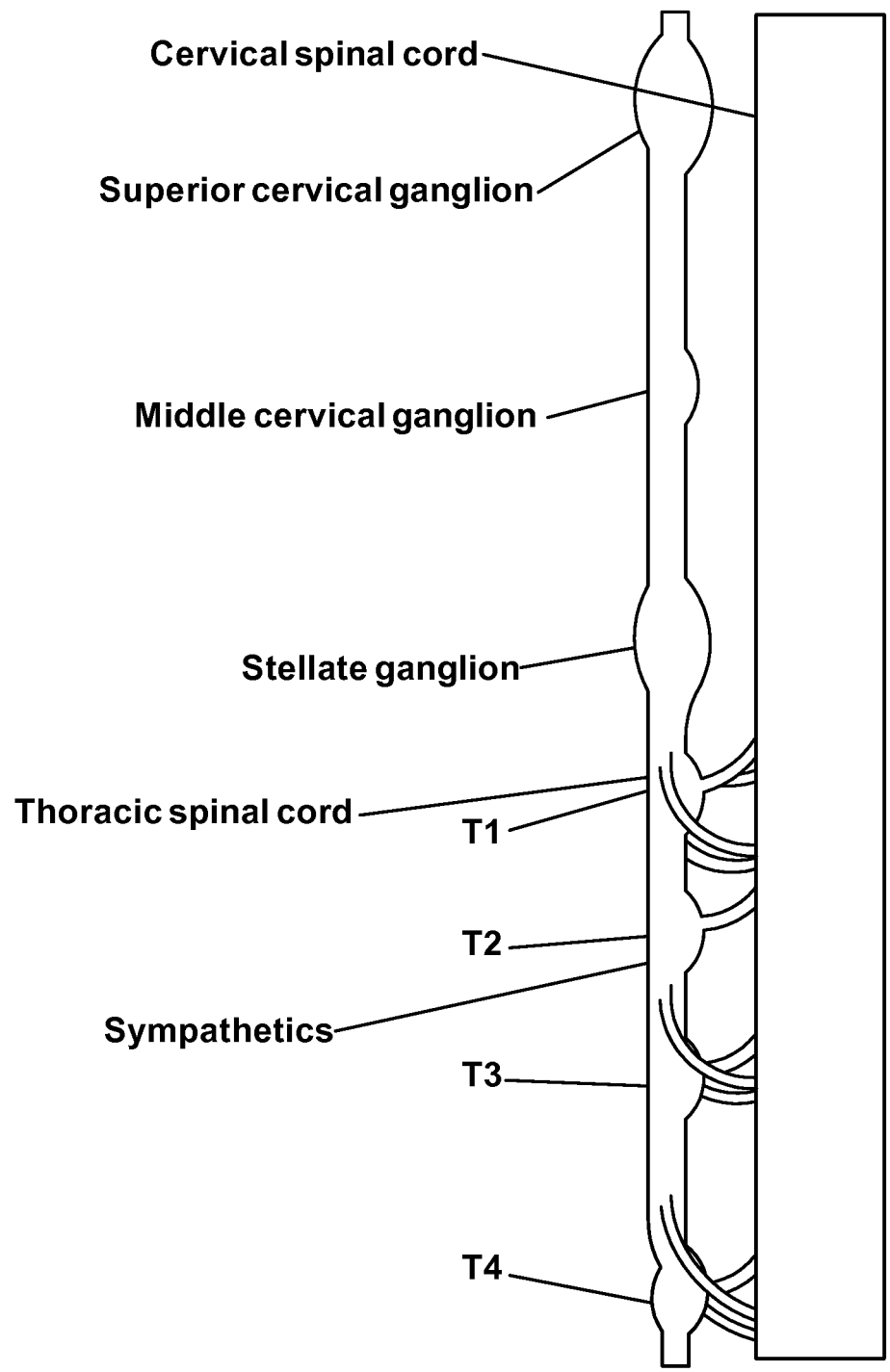
FIG. 1 is schematic illustration showing the cervical and upper thoracic portions of the sympathetic nerve chain and the spinal cord.

Unless defined otherwise, all technical and scientific terms used herein have the same meaning as is commonly understood by one of skill in the art to which the present disclosure pertains.

In the context of the present disclosure, the term "sympathetic nervous tissue" can refer to any tissues of the sympathetic nervous system (SNS) including, but not limited to, neurons, axons, fibers, tracts, nerves, plexus, afferent plexus fibers, efferent plexus fibers, ganglia, pre-ganglionic fibers, post-ganglionic fibers, cervical ganglia/ganglion (e.g., inferior, middle, and superior cervical ganglia), a cervicothoracic or stellate ganglion, and combinations thereof.

As used herein, the term "subject" can be used interchangeably with the term "patient" and refer to any warm-blooded organism including, but not limited to, human beings, pigs, rats, mice, dogs, goats, sheep, horses, monkeys, apes, farm animals, livestock, rabbits, cattle, etc.

As used herein, the terms "modulate" or "modulating" with reference to an autonomic nervous tissue or spinal nervous tissue can refer to causing a change in neuronal activity, chemistry and/or metabolism. The change can refer to an increase, decrease, or even a change in a pattern of neuronal activity. The terms may refer to either excitatory or inhibitory stimulation, or a combination thereof, and may be at least electrical, magnetic, ultrasound, optical, chemical, or a combination of two or more of these. The terms "modulate" or "modulating" can also be used to refer to a masking, altering, overriding, or restoring of neuronal activity.

As used herein, the terms "substantially blocked" or "substantially block" when used with reference to nervous tissue activity can refer to a complete (e.g., 100%) or partial inhibition (e.g., less than 100%, such as about 90%, about 80%, about 70%, about 60%, or less than about 50%) of nerve conduction through the nervous tissue.

As used herein, the term "activity" when used with reference to sympathetic nervous tissue can, in some instances, refer to the ability of a sympathetic nerve, neuron, or fiber to conduct, propagate, and/or generate an action potential. In other instances, the term can refer to the frequency at which a nerve or neuron is conducting, propagating, and/or generating one or more action potentials at a given moment in time. In further instances, the term can refer to the frequency at which a nerve or neuron is conducting, propagating, and/or generating one or more action potentials over a given period of time (e.g., seconds, minutes, hours, days, etc.).

As used herein, the term "electrical communication" can refer to the ability of an electric field generated by an electrode or electrode array to be transferred, or to have a neuromodulatory effect, within and/or on sympathetic nervous tissue.

As used herein, the term "menopause-related condition" can refer to any disease, disorder, sign, and/or symptom that is/are related to, caused at least in part by, and/or correlated with menopause. Menopause is generally defined as the last natural menstrual period, and is characterized by the cessation of ovarian function, leading to the substantial diminution of circulating estrogen in the bloodstream. Menopause can also be associated with conditions of decreased estrogen production that may be caused by surgical means, chemical means, and/or a disease state that leads to premature diminution or cessation of ovarian function. Non-limiting examples of menopause-related conditions can include cardiovascular disease (e.g., hypertension, high cholesterol), vasomotor symptoms including hot flashes, vaginal or vulvar atrophy, myalgia, arthralgia, atrophic vaginitis, vaginal dryness, pruritus, dyspareunia, dysuria, insomnia, irritability, frequent urination, urinary incontinence, urinary tract infections, dysfunctional uterine bleeding, infertility, osteoarthritis, bone weakness, brittleness or osteoporosis, memory loss, depression, etc., and other disease processes that many women begin to experience or begin to develop during the menopausal period.

As used herein, the terms "hot flash", "hot flush", and "night sweats" can be used interchangeably to refer to events that impact blood vessel diameter and are characterized by the sudden onset of intense warmth that typically begins in the chest and progresses to the neck and face. Hot flashes are often accompanied with palpitations, profuse sweating, and red blotching of the skin. A hot flash can begin when portions of the brain that control body temperature begin to react to various issues, such as a drop in hormone level, effect of chemotherapy, etc. The brain's insular cortex, which controls perceptions of heat, cold, pain and pleasure, is then activated. The core body temperature begins to rise in reaction to this activation. The temperature rises due to dilation of blood vessels and increased blood flow, which can result in dizziness and anxiety. The affected individual feels intensely hot, primarily in the upper portions of his or her body. The sweat glands activate and blood rushes to the extremities and face, neck and chest. The peripheral blood vessels dilate and heat shoots throughout the body, causing sweats.

As used herein, the terms "treat" or "treating" can refer to therapeutically regulating, preventing, improving, alleviating the symptoms of, and/or reducing the effects of a menopause-related condition in a subject, such as a peri-menopausal, menopausal, or postmenopausal subject. As such, treatment also includes situations where a menopause-related condition, or at least a symptom associated therewith, is completely inhibited, e.g., prevented from happening or stopped (e.g., terminated) such that the subject no longer suffers from the menopause-related condition, or at least the symptoms that characterize the menopause-related condition.

As used herein, the term "in communication" can refer to at least a portion of a therapy delivery device being adjacent, in the general vicinity, in close proximity, or directly next to and/or directly on or in a target site of the SNS (e.g., sympathetic nervous tissue) associated with a menopause-related condition. In some instances, the term can mean that at least a portion of a therapy delivery device or therapy delivery system is "in communication" with a target site of the SNS if application of a therapy signal (e.g., an electrical and/or chemical signal) thereto results in a modulation of neuronal activity to elicit a desired response, such as modulation of a sign or symptom associated with a menopause-related condition.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature may not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures.

It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

Overview

A brief discussion of the pertinent neurophysiology is provided to assist the reader with understanding certain aspects of the present disclosure.

The nervous system is divided into the somatic nervous system and the autonomic nervous system (ANS). In general, the somatic nervous system controls organs under voluntary control (e.g., skeletal muscles) and the ANS controls individual organ function and homeostasis. For the most part, the ANS is not subject to voluntary control. The ANS is also commonly referred to as the visceral or automatic system.

The ANS can be viewed as a "real-time" regulator of physiological functions which extracts features from the environment and, based on that information, allocates an organism's internal resources to perform physiological functions for the benefit of the organism, e.g., responds to environment conditions in a manner that is advantageous to the organism. The ANS acts through a balance of its two components: the SNS and the parasympathetic nervous system (PNS), which are two anatomically and functionally distinct systems. Both of these systems include myelinated preganglionic fibers which make synaptic connections with unmyelinated postganglionic fibers, and it is these fibers which then innervate the effector structure. These synapses usually occur in clusters called ganglia. Most organs are innervated by fibers from both divisions of the ANS, and the influence is usually opposing (e.g., the vagus nerve slows the heart, while the sympathetic nerves increase its rate and contractility), although it may be parallel (e.g., as in the case of the salivary glands). Each of these is briefly reviewed below.

The SNS is the part of the ANS comprising nerve fibers that leave the spinal cord in the thoracic and lumbar regions and supply viscera and blood vessels by way of a chain of sympathetic ganglia (also referred to as the sympathetic chain, sympathetic trunk or the gangliated cord) running on each side of the spinal column, which communicate with the central nervous system via a branch to a corresponding spinal nerve. The sympathetic trunks extend from the base of the skull to the coccyx. The cephalic end of each is continued upward through the carotid canal into the skull, and forms a plexus on the internal carotid artery; the caudal ends of the trunks converge and end in a single ganglion, the ganglion impar, placed in front of the coccyx.

The SNS controls a variety of autonomic functions including, but not limited to, control of movement and secretions from viscera and monitoring their physiological state, stimulation of the sympathetic system inducing, e.g., the contraction of gut sphincters, heart muscle and the muscle of artery walls, and the relaxation of gut smooth muscle and the circular muscles of the iris. The chief neurotransmitter in the SNS is adrenaline, which is liberated in the heart, visceral muscle, glands and internal vessels, with acetylcholine acting as a neurotransmitter at ganglionic synapses and at sympathetic terminals in skin and skeletal muscles. The actions of the SNS tend to be antagonistic to those of the PNS.

As partly shown in FIG. 1, the ganglia of each trunk are distinguished as cervical, thoracic, lumbar, and sacral and, except in the neck, they closely correspond in number to the vertebrae. The cervical ganglia are paravertebral ganglia of the SNS. These emerging postganglionic nerves synapse with preganglionic nerves from the thoracic spinal cord. They consist of three paravertebral ganglia: the superior cervical ganglion; the middle cervical ganglion; and the inferior cervical ganglion. The inferior ganglion may be fused with the first thoracic ganglion to form a single structure, the stellate ganglion.

The neurotransmitter released by the post-ganglionic neurons is nonadrenaline (also called norepinephrine). The action of noradrenaline on a particular structure, such as a gland or muscle, is excitatory in some cases and inhibitory in others. At excitatory terminals, ATP may be released along with noradrenaline. Activation of the SNS may be characterized as general because a single pre-ganglionic neuron usually synapses with many post-ganglionic neurons, and the release of adrenaline from the adrenal medulla into the blood ensures that all the cells of the body will be exposed to sympathetic stimulation even if no post-ganglionic neurons reach them directly.

The present disclosure relates generally to neuromodulatory devices, systems and methods, and more particularly to devices, systems, and methods for neuromodulation of the SNS to treat menopause-related conditions. Neuromodulation according to the present disclosure can improve the function, activate, inhibit, modulate, and impact the SNS, as well as normalize or regulate the function and sympathetic output to impact menopause-related conditions. As described in detail below, the present disclosure can advantageously provide, in some instances, devices, systems, and methods for uncoupling dysfunctional nerve signals from the brain to the SNS (as well as ascending signals into the central nervous system), as well as dysfunctional nerve signals from the SNS to peripheral tissues to effectively treat menopause-related conditions.

Therapy Delivery Devices and Systems

In one aspect, the present disclosure can include various therapy delivery devices and related systems (not shown) configured to treat one or more menopause-related conditions in a subject. In some instances, therapy delivery devices that may be used to practice the present disclosure may be positioned substantially adjacent (e.g., directly adjacent) a target site of the SNS associated with a menopause-related condition. In other instances, therapy delivery devices used to practice the present disclosure can comprise an external device configured for placement on the skin of a subject substantially adjacent (e.g., directly adjacent) a target site of the SNS that is associated with a menopause-related condition. Therapy delivery devices can be temporarily or permanently implanted within, on, or otherwise associated with a subject suffering from, afflicted by, or suspected of having a menopause-related condition.

Therapy delivery devices of the present disclosure can be configured to deliver various types of therapy signals to SNS nerve targets (e.g., sympathetic nervous tissue) associated with a menopause-related condition. For example, therapy delivery devices of the present disclosure can be configured to deliver only electrical energy, only magnetic energy, only a pharmacological or biological agent, or a combination thereof. In one example, therapy delivery devices of the present disclosure can comprise at least one electrode and an integral or remote power source, which is in electrical communication with the electrode(s) and configured to produce one or more therapy signals (e.g., electrical energy or pulses). In another example, therapy delivery devices can include a pharmacological or biological agent reservoir, a pump, and a fluid dispensing mechanism. Non-limiting examples of pharmacological and biological agents can include chemical compounds, drugs (e.g., prazosin, clonidine), nucleic acids, polypeptides, stem cells, toxins (e.g., botulinum), as well as various energy forms, such as ultrasound, radiofrequency (continuous or pulsed), magnetic waves, cryotherapy, and the like. One skilled in the art will appreciate that combinations of therapy delivery devices discussed herein are also included within the scope of the present disclosure.

In some instances, therapy delivery devices can comprise a stimulator (or inhibitor), such as an electrode, a controller or programmer, and one or more connectors (e.g., leads) for connecting the stimulating (or inhibiting) device to the controller. Each component of the therapy delivery devices can be in electrical communication with one another (e.g., via a physical connection, such as a lead or wire, or a wireless link). In further describing representative electrodes, which are described in the singular, it will be apparent that more than one electrode may be used as part of a therapy delivery device. Accordingly, the description of a representative electrode suitable for use in the therapy delivery devices of the present disclosure is applicable to other electrodes that may be employed.

An electrode can be controllable to provide output signals that may be varied in voltage, frequency, pulse-width, current and intensity. The electrode can also provide both positive and negative current flow from the electrode and/or be capable of stopping current flow from the electrode and/or change the direction of current flow from the electrode. In some instances, therapy delivery devices can include an electrode that is controllable, i.e., in regards to producing positive and negative current flow from the electrode, stopping current flow from the electrode, changing direction of current flow from the electrode, and the like. In other instances, the electrode has the capacity for variable output, linear output and short pulse-width, as well as paired pulses and various waveforms (e.g., sine wave, square wave, and the like). The electrode can be sized and dimensioned for application to a particular target site of the SNS. For example, the electrode can be sized and dimensioned for application to one (e.g., only one) or more sympathetic cervical ganglia.

The power source can comprise a battery or generator, such as a pulse generator that is operatively connected to an electrode via the controller. The power source can be configured to generate an electrical signal or signals. In one example, the power source can include a battery that is rechargeable by inductive coupling. Other forms of energy, such as microwave, ultrasound, or light can alternatively be used for inductive coupling. The power source may be positioned in any suitable location, such as adjacent the electrode (e.g., implanted adjacent the electrode), or a remote site in or on the subject's body or away from the subject's body in a remote location. An electrode may be connected to the remotely positioned power source using wires (e.g., which may be implanted at a site remote from the electrode(s)), or be positioned outside the subject's body. In some instances, an electrode may be employed that includes its own power source, e.g., which is capable of obtaining sufficient power for operation from surrounding tissues in the subject's body, or which may be powered by bringing a power source external to the subject's body into contact with the subject's skin, or which may include an integral power source.

The controller can be configured to control the pulse waveform, the signal pulse width, the signal pulse frequency, the signal pulse phase, the signal pulse polarity, the signal pulse amplitude, the signal pulse intensity, the signal pulse duration, and/or combinations thereof, of a therapy signal (e.g., an electrical signal). The controller may be used to convey a variety of currents and voltages to one or more electrodes and thereby modulate the activity of a target sympathetic nervous tissue. The controller may be used to control numerous electrodes independently or in various combinations as needed to provide stimulation (e.g., inhibition) of sympathetic nerve activity. In some instances, the controller can form part of an implantable or external therapy delivery device, e.g., contained within a housing of the therapy delivery device. In other instances, the controller can form or be associated with a remote electronic device (e.g., a smart phone) that is in electrical communication with the therapy delivery device. In such instances, the controller of the remote electronic device may be in electrical communication with a second controller, which forms part of the therapy delivery device.

Electrical signal (or signals) delivered by the controller to the electrode may be constant, varying and/or modulated with respect to the current, voltage, pulse-width, cycle, frequency, amplitude, and so forth. For example, a current may range from about 0.001 to about 1000 microampere (mA) and, more specifically, from about 0.1 to about 100 mA. Similarly, the voltage may range from about 0.1 millivolt to about 25 volts, or about 0.5 to about 4000 Hz (e.g., about 20 Hz), with a pulse-width of about 10 to about 1000 microseconds (e.g., about 400 microseconds). In one example, the electrical signal can be oscillatory. The type of stimulation may vary and involve different waveforms known to the skilled artisan. For example, the stimulation may be based on the H waveform found in nerve signals (i.e., Hoffman Reflex). In another example, different forms of interferential stimulation may be used.

To decrease activity in sympathetic nervous tissue comprising a target site of the SNS, for example, voltage or intensity may range from about 1 millivolt to about 1 volt or more, e.g., 0.1 to about 50 mA or volts (e.g., from about 0.2 s volt to about 20 volts), and the frequency may range from about 1 Hz to about 2500 Hz, e.g., about 20 Hz. In one example, an electrical signal can have a frequency range of about 10,000 Hz or greater (e.g., high frequency stimulation) to effectively block nerve conduction. In some instances, pure DC and/or AC voltages may be employed. The pulse-width may range from about 1 microseconds to about 10,000 microseconds or more, e.g., about 400 microseconds. The electrical signal may be applied for at least about 1 millisecond or more, e.g., about 1 second (e.g., about several seconds). In some instances, the electrical energy may be applied for as long as about 1 minute or more, e.g., about several minutes or more (e.g., about 30 minutes or more may be used).

The electrode may be mono-polar, bipolar or multi-polar. To minimize the risk of an immune response triggered by the subject against the therapy delivery device, and also to minimize damage thereto (e.g., corrosion from other biological fluids, etc.), the electrode (and any wires and optional housing materials) can be made of inert materials, such as silicon, metal, plastic, and the like. In one example, a therapy delivery device can include a multi-polar electrode having about four exposed contacts (e.g., cylindrical contacts).

As discussed above, the controller (or a programmer) may be associated with a therapy delivery device. The controller can include, for example, one or more microprocessors under the control of a suitable software program. Other components of a controller, such as an analog-to-digital converter, etc., will be apparent to those of skill in the art. In some instances, the controller can be configured to record and store data indicative of sympathetic activity in the subject (e.g., at a target site of the SNS). Therefore, the controller can be configured to apply one or more electrical signals to the electrode when the intrinsic sympathetic tone or activity of a SNS target site increases or decreases above (or below) a certain threshold value (or range of values), such as a normal or baseline level.

Therapy delivery devices can be pre-programmed with desired stimulation parameters (e.g., frequencies and intensities). In some instances, stimulation parameters can be controllable so that an electrical signal may be remotely modulated to desired settings without removal of the therapy delivery device from its target position. Remote control may be performed using, for example, conventional telemetry with an implanted power source, an implanted radiofrequency receiver coupled to an external transmitter, and the like. In other instances, stimulation parameters can be pre-programmed so that therapy signals are automatically applied to a target site of the SNS at a desired frequency and intensity. For example, stimulation parameters can be pre-programmed to apply blocking stimulation to a target site of the SNS over a desired period of time, such as only a nighttime or only during the daytime. In some instances, some or all parameters of the therapy delivery device may be controllable by the subject, e.g., without supervision by a physician.

In one example, the therapy delivery device can be configured for intravascular placement or implantation. In some instances, a therapy delivery device configured for intravascular placement or implantation can be configured in an identical or similar manner as the expandable electrode disclosed in U.S. patent application Ser. No. 11/641,331 to Greenberg et al. (hereinafter, "the '331 application"). In one example, the therapy delivery device can be configured for intravascular placement or implantation at an implantation site that is adjacent, or directly adjacent, a target site of the SNS, such as one (e.g., only one) or more sympathetic cervical ganglia.

In another example, the therapy delivery device can be configured for transcutaneous neuromodulation. In some instances, transcutaneous neuromodulation can include positioning a therapy delivery device on a skin surface so that a therapy signal (e.g., an electrical signal or magnetic field) can be delivered to a SNS nerve target associated with a menopause-related condition. Transcutaneous neuromodulation can additionally include partially transcutaneous methods (e.g., using a fine, needle-like electrode to pierce the epidermis). In one example, an electrical signal used for transcutaneous neuromodulation may be constant, varying, and/or modulated with respect to the current, voltage, pulse-width, cycle, frequency, amplitude, and so forth (e.g., the current may be between about 1 to 100 microampere), about 10 V (average), about 1 to about 1000 Hz or more, with a pulse-width of about 250 to about 500 microseconds.

In yet another example, the therapy delivery device can be configured for implantation within a subject. Implantation of a therapy delivery device can be performed using a percutaneous or minimally invasive surgical approach. Examples of devices that may be suitable for implantation as a therapy delivery device according to the present disclosure are disclosed by U.S. Patent Publication No. 2013/0013023 A1 and U.S. Pat. Nos. 8,583,229 and 7,477,945.

Methods

Another aspect of the present disclosure includes methods for treating a menopause-related condition in a subject. Examples of menopause-related conditions treatable by the present disclosure are provided above. Subjects treatable by the present disclosure can, in some instances, be diagnosed with (or suspected of having) a menopause-related condition and, optionally, one or more related or unrelated medical conditions. In some instances, a therapy delivery device can be placed into electrical communication with a target site of the SNS (e.g., sympathetic nerve tissue) associated with the menopause-related condition. As discussed in more detail below, this can be done via an intravascular, transdermal (transcutaneous), or percutaneous surgical approach. Examples of SNS nerve targets into which a therapy delivery device may be placed into electrical communication with can include, but are not limited to, any tissues of the SNS, such as a sympathetic chain ganglion, an efferent of a sympathetic chain ganglion, or an afferent of a sympathetic chain ganglion, a cervical sympathetic ganglion (e.g., an upper or superior cervical sympathetic ganglion, a middle cervical sympathetic ganglion, a lower or inferior cervical sympathetic ganglion, or a stellate ganglion). It will be appreciated that, in some instances, it may be desirable to place a therapy delivery device into electrical communication with only one particular sympathetic nervous tissue or nerve structure (e.g., only one of an inferior, middle, superior or stellate ganglion) where certain therapeutic advantages are realized by doing so.

After placing the therapy delivery device, the therapy delivery device can be activated to deliver a therapy signal to the target site of the SNS. In some instances, delivery of a therapy signal to the target site of the SNS can prevent a sign and/or symptom associated with the menopause-related condition from either increasing or decreasing (as compared to a control or baseline). In other instances, delivery of a therapy signal to the target site of the SNS can cause a sign and/or symptom associated with the menopause-related condition to decrease (as compared to a control or baseline). The therapy delivery device can be activated at the onset of an episode (e.g., the onset of a sign and/or symptom) associated with the menopause-related condition or, alternatively, the therapy delivery device can be activated continuously or intermittently to reduce or eliminate the frequency of such episode(s).

Delivery of the therapy signal(s) to the target site of the SNS can affect central motor output, nerve conduction, neurotransmitter release, synaptic transmission, and/or receptor activation at one or more associated target tissues (e.g., the skin, heart, brain, etc.). In some instances, delivery of a therapy signal (e.g., an electrical signal) to the target site of the SNS can substantially block (e.g., partially block) activity of the sympathetic nervous tissue comprising the target site for a desired period of time. In other instances, delivery of a therapy signal (e.g., an electrical signal) to the target site of the SNS can achieve a complete nerve conduction block of sympathetic nervous tissue comprising the target site for a desired period of time. Prior art methods for delivering electrical signals to sympathetic nervous tissue (e.g., the stellate ganglion) include application of pulsed radiofrequency (PRF) to reduce sympathetic activity. PRF is characterized by delivery of high-intensity current in pulses; during each cycle, an active phase is followed by a silent phase. Although PRF increases the temperature of the target tissue, the silent phase allows heat to dissipate so that neurodestructive temperatures are not reached. PRF does not provide a continuous reduction or blockade of nerve activity, however, since current is not applied during the silent phase. Advantageously, one example of the present disclosure can include continuous application of an electrical signal that substantially blocks or reduces sympathetic nerve activity without an increase in temperature of the target sympathetic nervous tissue. The degree to which sympathetic activity is modulated (e.g., decreased) can be titrated by one skilled in the art depending, for example, upon the nature and severity of the menopause-related condition.

Figure 2:
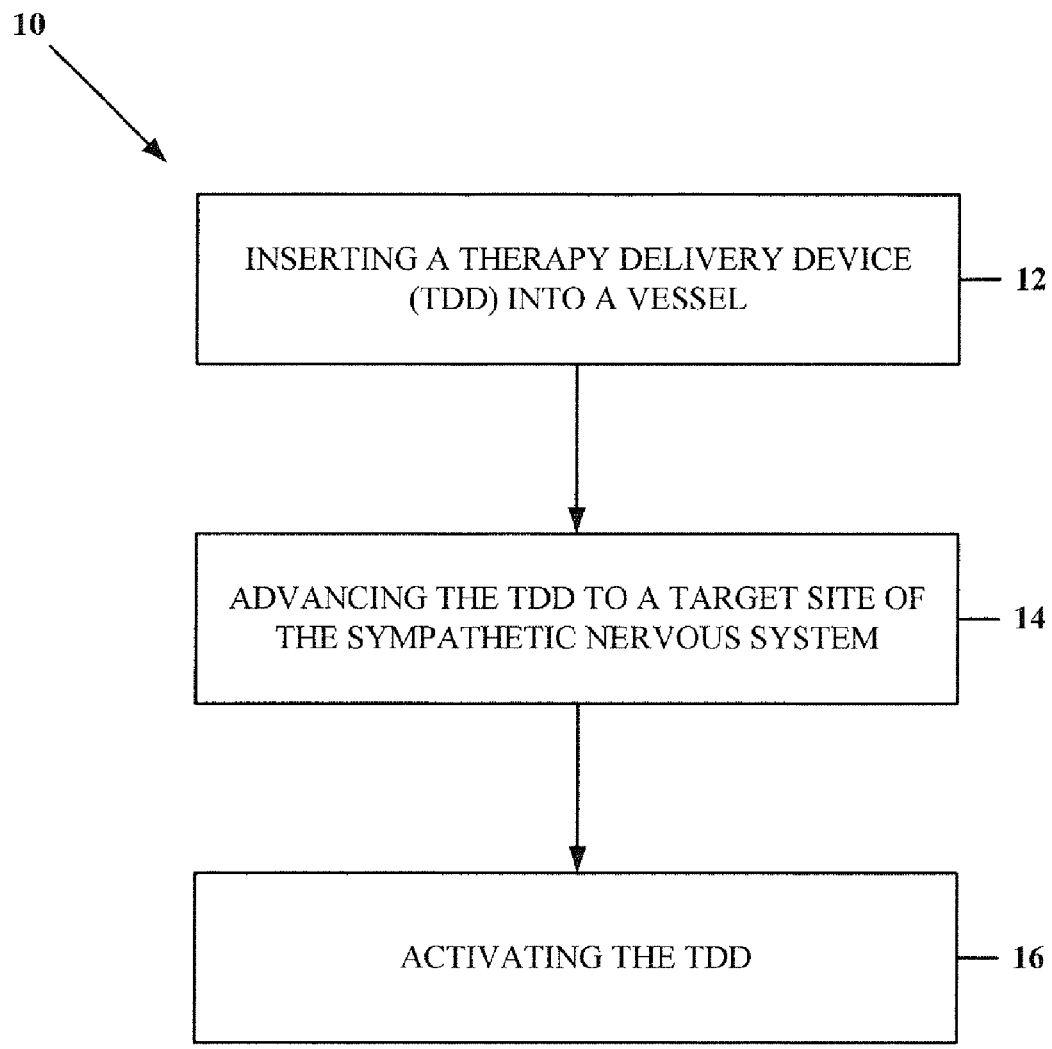
FIG. 2 is a process flow diagram illustrating a method for treating a menopause-related condition in a subject according to one aspect of the present disclosure.

In one example of the present disclosure, a method 10 (FIG. 2) is provided for treating a menopause-related condition, such as hot flashes, via a transvascular approach. Thus, in some instances, the method 10 can include providing a therapy delivery device (or system) configured for transvascular insertion and placement of the therapy delivery device (or system) within the subject. In one example, a therapy delivery device configured for intravascular placement in a subject can include an expandable electrode as disclosed in the '331 application. At Step 12 of the method 10, the therapy delivery device can be inserted into a vessel of the subject. The vessel can comprise a vein or artery. Non-limiting examples of vessels into which the therapy delivery device can be inserted include an intercostal vein, an intercostal artery, and a right or left subclavian artery. In one example, an intravascular therapy delivery device (or devices) can be positioned in an intercostal vein, an intercostal artery, a right subclavian artery, and/or a left subclavian artery so that it is adjacent (e.g., directly adjacent), and in electrical communication with, the stellate ganglion. The therapy delivery device can be surgically inserted into the vessel via a percutaneous (e.g., minimally invasive), transvascular, or open surgical procedure.

After inserting the therapy delivery device into the vessel, the therapy delivery device can be advanced (if needed) to a point substantially adjacent (e.g., directly adjacent) a target site of the SNS associated with hot flashes (Step 14). In some instances, advancement of the therapy delivery device can be done under image guidance (e.g., fluoroscopy, CT, MRI, etc.). The therapy delivery device can be positioned within the vessel so that it is in electrical communication with the target site of the SNS. For example, the therapy delivery device can be positioned within the vessel so that one or more electrodes of the therapy delivery device are adjacent (e.g., directly adjacent) a portion of the vessel wall that is innervated by (or in electrical communication with) sympathetic nervous tissue comprising the target site of the SNS. In one example, the sympathetic nervous tissue comprising the target site of the SNS can include a cervical ganglion, such as a superior, middle, inferior or stellate ganglion.

At Step 16, the therapy delivery device can be activated to deliver a therapy signal (e.g., in a continuous or periodic manner) to the target site of the SNS in an amount and for a time sufficient to effect a change (e.g., decrease) in sympathetic activity in the sympathetic nervous tissue comprising the target site. The manner in which the therapy signal(s) is/are delivered to the target site of the SNS will depend upon the configuration of therapy delivery device, the acuity of hot flashes experienced by the subject, the general health of the subject (e.g., any co-morbid conditions), etc. In some instances, the therapy delivery device can be programmed (e.g., prior to insertion into the subject) so that the therapy signal is automatically delivered to the target site of the SNS at a pre-determined frequency and intensity. In other instances, the subject can selectively trigger activation of the therapy delivery device by inductively coupling the device to a power source (e.g., at the onset of a hot flash). The therapy signal can be delivered in an amount and for a time sufficient to effectively prevent, suppress, or eliminate the hot flash(es).

Figure 3:
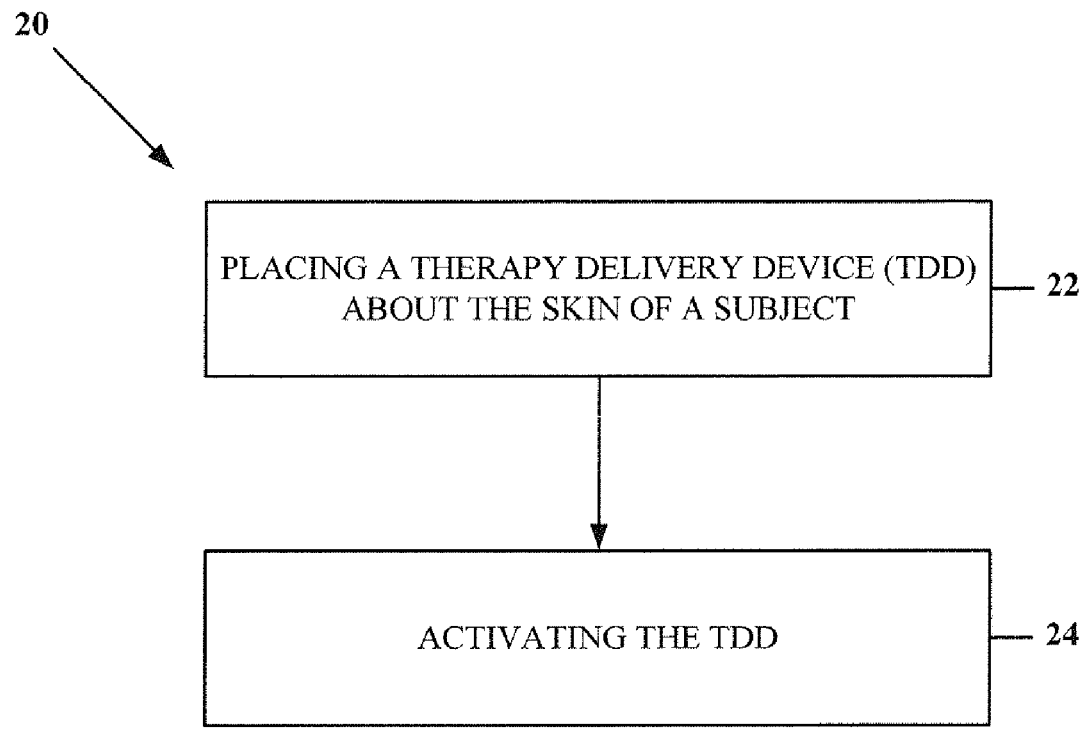
FIG. 3 is a process flow diagram illustrating a method for treating a menopause-related condition in a subject according to another aspect of the present disclosure.

In another example of the present disclosure, a method 20 (FIG. 3) is provided for treating a menopause-related condition, such as hot flashes, via a transdermal or transcutaneous approach. At Step 22, a therapy delivery device (or system) can be positioned about the subject, without penetrating the skin of the subject, so that the therapy delivery device is in electrical communication with a target site of the SNS associated with hot flashes. For example, the therapy delivery device can be placed into direct contact with the skin of the subject that overlies the target site of the SNS (e.g., a portion of the subject's neck). Non-limiting examples of SNS nerve targets into which the therapy delivery device can be placed into electrical communication are described above.

At Step 24, the therapy delivery device can be activated so that a therapy signal (or signals) is/are delivered to the target site of the SNS in an amount and for a time sufficient to effect a change (e.g., decrease) in sympathetic activity in the sympathetic nervous tissue comprising the target site. The manner in which the therapy signal(s) is/are delivered to the target site of the SNS will depend upon the configuration of therapy delivery device, the acuity of hot flashes experienced by the subject, the general health of the subject (e.g., any co-morbid conditions), etc. In some instances, the therapy delivery device can be programmed so that the therapy signal is automatically delivered to the target site of the SNS at a predetermined frequency and intensity when, for example, the therapy delivery device is placed into contact with the skin of the subject. In other instances, the subject can selectively trigger activation of the therapy delivery device by actuating a "START" button of the device (e.g., at the onset of a hot flash). The therapy signal can be delivered in an amount and for a time sufficient to effectively prevent, suppress, or eliminate the hot flash(es).

Figure 4:
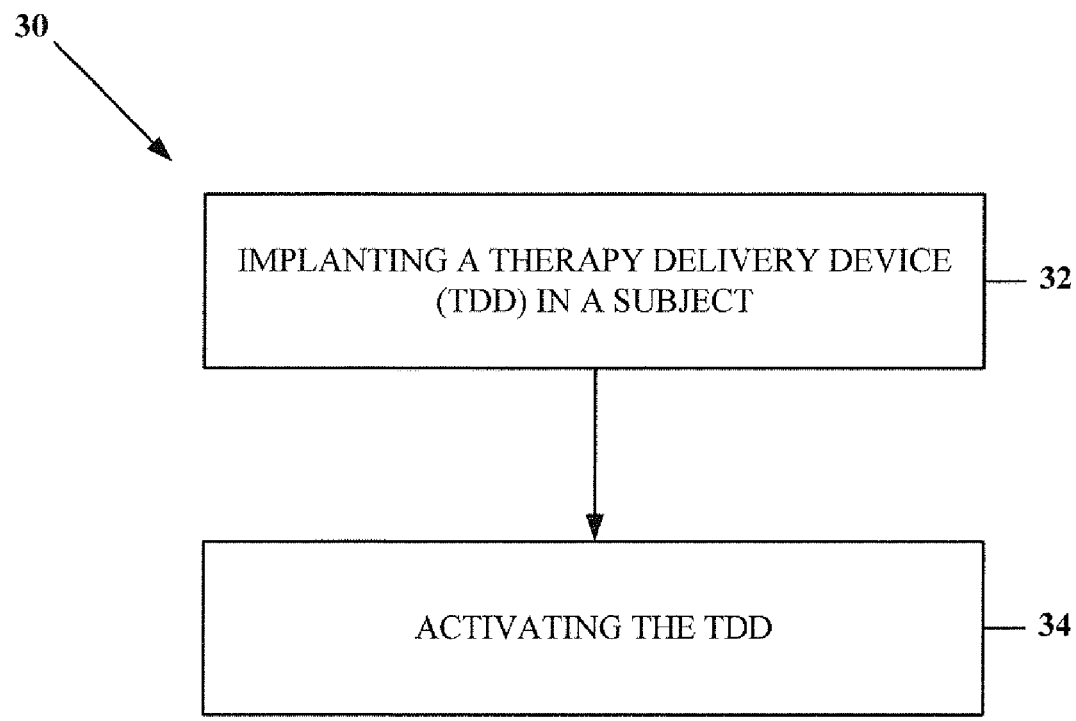
FIG. 4 is a process flow diagram illustrating a method for treating a menopause-related condition in a subject according to one aspect of the present disclosure.

In another example of the present disclosure, a method 30 (FIG. 4) is provided for treating a menopause-related condition, such as hot flashes, via a percutaneous, minimally invasive, or open surgical approach. At Step 32, a therapy delivery device can be implanted in the subject. In one example, the therapy delivery device can comprise an electrode array configured for percutaneous implantation. In some instances, the therapy delivery device can be placed into direct electrical contact with a target site of the SNS, such as a cervical ganglion. "Direct electrical contact" can mean that at least a portion of the therapy delivery device is placed on or in sympathetic nervous tissue comprising the target site. In other instances, the therapy delivery device can be placed into indirect electrical contact with a target site of the SNS. "Indirect electrical contact" can mean that the therapy delivery device is located adjacent or directly adjacent (but not in physical contact with) sympathetic nervous tissue comprising the target site such that delivery of a therapy signal (e.g., an electrical signal) thereto can modulate a function, activity, and/or characteristic of the sympathetic nervous tissue.

After placing the therapy delivery device into electrical contact with the target site of the SNS, the therapy delivery device can be activated to deliver a therapy signal (or signals) (e.g., in a continuous or periodic manner) to the target site of the SNS in an amount and for a time sufficient to effect a change (e.g., decrease) in sympathetic activity in the sympathetic nervous tissue comprising the target site (Step 34). The manner in which the therapy signal(s) are delivered to the target site of the SNS will depend upon the configuration of therapy delivery device, the acuity of hot flashes experienced by the subject, the general health of the subject (e.g., any co-morbid conditions), etc. In some instances, the therapy delivery device can be programmed (e.g., prior to implantation into the subject) so that the therapy signal is automatically delivered to the target site of the SNS at a pre-determined frequency and intensity. In other instances, the subject can selectively trigger activation of the therapy delivery device by inductively coupling the device to a power source (e.g., at the onset of a hot flash). The therapy signal can be delivered in an amount and for a time sufficient to effectively prevent, suppress, or eliminate the hot flash(es).

From the above description of the present disclosure, those skilled in the art will perceive improvements, changes and modifications. Such improvements, changes, and modifications are within the skill of those in the art and are intended to be covered by the appended claims. All patents, patent applications, and publication cited herein are incorporated by reference in their entirety.

The following is claimed:

1. A method for treating a menopause-related condition in a subject, the method comprising the steps of:
   receiving a therapy delivery device in a vessel of the subject at a point substantially adjacent a target site of the sympathetic nervous system (SNS) that is associated with the menopause-related condition; and
   activating the therapy delivery device, wherein the therapy delivery device is configured to deliver a therapy signal to the target site of the SNS in an amount and for a time sufficient to substantially block sympathetic activity in the subject and thereby treat the menopause-related condition, wherein the menopause-related condition is hot flashes.

2. The method of claim 1, wherein the target site of the SNS is a cervical ganglion.

3. The method of claim 1, wherein the therapy delivery device is configured to automatically deliver the therapy signal to the target site of the SNS at a pre-determined frequency and intensity.

4. The method of claim 1, wherein the activating step comprises inductively coupling the therapy delivery device to a power source.

5. The method of claim 1, wherein the vessel is one of an intercostal vein, an intercostal artery, or a subclavian artery.

6. A method for treating a menopause-related condition in a subject, the method comprising the steps of:
   receiving a therapy delivery device in the subject so that the therapy delivery device is in electrical contact with a target site of the SNS associated with the menopause-related condition; and
   activating the therapy delivery device, wherein the therapy delivery device is configured to deliver a therapy signal to the target site of the SNS in an amount and for a time sufficient to substantially block sympathetic activity in the subject and thereby treat the menopause-related condition, wherein the menopause-related condition is hot flashes.

7. The method of claim 6, wherein the target site of the SNS is a cervical ganglion.

8. The method of claim 6, wherein the therapy delivery device is configured to automatically deliver the therapy signal to the target site of the SNS at a pre-determined frequency and intensity.

9. The method of claim 6, wherein the activating step comprises inductively coupling the therapy delivery device to a power source.

* * * * *